United States Patent [19]

Boozalis et al.

[11] 3,989,601
[45] Nov. 2, 1976

[54] PURIFICATION OF 1,1,1-TRICHLOROETHANE BY EXTRACTIVE DISTILLATION

[75] Inventors: Theodore S. Boozalis; John B. Ivy; Gordon G. Willis, all of Lake Jackson, Tex.

[73] Assignee: The Dow Chemical Company, Midland, Mich.

[22] Filed: Sept. 8, 1975

[21] Appl. No.: 611,390

[52] U.S. Cl. .................................. 203/61; 203/63; 260/652 P
[51] Int. Cl.$^2$ ......................................... B01D 3/40
[58] Field of Search .............. 203/61, 63; 260/652 P

[56] References Cited
UNITED STATES PATENTS

| | | | |
|---|---|---|---|
| 2,106,158 | 1/1938 | Povenz et al. | 260/652 P |
| 3,113,079 | 12/1963 | Bergeron et al. | 260/652 P |
| 3,282,801 | 11/1966 | Wiist | 203/63 |
| 3,658,658 | 4/1972 | Bursack et al. | 203/63 |

Primary Examiner—Norman Yudkoff
Assistant Examiner—J. Sofer
Attorney, Agent, or Firm—A. Cooper Ancona

[57] ABSTRACT

1,1,1-Trichloroethane containing 1,2-dichloroethane as a principal contaminant is purified by extractive distillation, employing as an extraction solvent a saturated or unsaturated tertiary $C_4$ to $C_7$ alcohol, e.g., t-amyl alcohol, 2-methyl-3-buten-2-ol or 2-methyl-3-butyn-2-ol, or mixtures thereof, organic monocarboxylic acids and organic monocarboxylic acid anhydrides.

6 Claims, No Drawings

PURIFICATION OF 1,1,1-TRICHLOROETHANE BY EXTRACTIVE DISTILLATION

BACKGROUND OF THE INVENTION

A commercially employed process for the preparation of 1,1,1-trichloroethane, a useful degreasing solvent, is that of thermally chlorinating a mixture of chlorohydrocarbons including primarily ethyl chloride and 1,1-dichloroethane. This method permits production of 1,1,1-trichloroethane from a mixed ethyl chloride-1,1-dichloroethane feed stream, the 1,1-dichloroethane being converted to 1,1,1-trichloroethane while simultaneously the ethyl chloride is converted to 1,1-dichloroethane which can be fed with fresh ethyl chloride back into reaction and further chlorinated to 1,1,1,-trichloroethane. Because 1,1,1-trichloroethane can be prepared without intense carbon formation and without large amounts and varieties of useless by-products, the process is of immense commercial interest, though nevertheless the process is subject to one severe limitation.

Though the simultaneous chlorination of ethyl chloride and 1,1-dichloroethane to produce 1,1,1-trichloroethane proceeds smoothly, efficiently and without excess carbon formation, a small amount of chlorinated by-products are produced in the reaction. Unfortunately, though the total quantity of these by-products is not very great, some of these chlorohydrocarbons cannot be separated from 1,1,1-trichloroethane without the necessity of using an extremely impractical number of distillation columns. The problem of separating 1,1,1-trichloroethane from other chlorohydrocarbons arises not only because of a closeness of boiling points between the 1,1,1-trichloroethane and the other chlorohydrocarbon compounds from which it is to be separated, but also because of a peculiar characteristic of 1,1,1-trichloroethane which causes the separation to become more and more difficult as the relative concentration of the 1,1,1-trichloroethane in the mixture is increased. For example, a very troublesome by-product from which to separate 1,1,1-trichloroethane is 1,2-dichloroethane. Thus to effect a commercially acceptable separation of 1,1,1-trichloroethane from 1,2-dichloroethane by distillation would require on the order of about 150 trays which, as a practical matter, means that several distillation columns must be used. In other words, in the usual commercial plant it is necessary to use four or five distillation columns or more. This requirement places an extremely heavy burden on the commercial use of the process of co-chlorinating ethyl chloride and 1,1-dichloroethane to manufacture 1,1,1-trichloroethane.

A solution to the problems encountered in purifying 1,1,1-trichloroethane particularly with reference to removal of 1,2-dichloroethane was suggested in U.S. Pat. No. 3,113,079 in which an extracting agent, an ether of phenol, having a melting point not greater than about 70° C and a boiling point at atmospheric pressure of at least 75° C, was added to the impure mixture which when distilled made possible the recovery of a distillate of 1,1,1-trichloroethane of 99 percent purity.

In a somewhat similar view U.S. Pat. No. 3,658,657 discloses the use of one or more of the following compounds:

tetrahydrofurfuryl alcohol or n-butyronitrile,
anisole, isobutyl acetate, epichlorohydrin or
a $C_2$ to $C_3$ nitroalkane.

These processes require removal of the extractive agent either because (1) the extractant is present in too high a concentration for subsequent use of the 1,1,1-trichloroethane as a commercial solvent or (2) the extractants detract from the use as a solvent of the 1,1,1-trichloroethane containing the same. The extractants suggested include compounds which are taught in the literature as inhibitors or acid acceptors, i.e., dioxane, the nitroalkanes, epichlorohydrin, and tetrahydrofurfuryl alcohol. When these are employed as the extractant they may be left in the distillate if they are present in a quantity to supplement the stabilizers normally employed. However, as is observed in the references cited above, the art compounds are not wholly satisfactory for one or more reasons. The table below shows the results reported in U.S. Pat. No. 3,658,657 as representative of the art:

| Patent Example | Distillation Column* | Extracting** Agent (rate) | Feed*** (wt. %) | Overhead (wt. %) | Bottoms (wt. %) |
|---|---|---|---|---|---|
| XVI | No. 1 Reflux = 3:1 | THFA 268 g/hr | 95.5 TCE 4.1 DCE | 98.7 TCE 0.8 DCE 0.5 THFA | 0.1 TCE 1.0 DCE 98.9 THFA |
| XVII | No. 2 Reflux = 4:1 | THFA 268 g/hr | same | 99.1 TCE 0.3 DCE 0.6 THFA | 1.8 TCE 12.5 DCE 85.7 THFA |
| XVIII | No. 3 Reflux = 5:1 | IBA 20,400 g/hr | 94.5 TCE 5.2 DCE 0.3 other chlorohydro- carbons | 99.26 TCE 0.27 DCE 0.002 IBA 0.47 other chlorohydro- carbons | — — — |

*Column 1 — 20-tray Oldershaw + 10-tray Brunn and feed inlet and liquid dividing head for control of reflux
Column No. 2 — 20-tray Oldershaw + 10-tray Oldershaw and feed inlet and liquid dividing head for control of reflux
Column No. 3 — 8-inch diameter Monel, 32-tray
**THFA = tetrahydrofurfuryl alcohol
= isobutyl acetate
***TCE = 1,1,1-trichloroethane
DCE = 1,2-dichloroethane It can be seen from the above that the dichloroethane and other chlorinated hydrocarbons are incompletely removed from the 1,1,1-trichloroethane.

According to the present invention it has been found that the deficiencies of the prior art can be overcome by employing as the extractive solvent in an extractive distillation for separating 1,1,1-trichloroethane from 1,2-dichloroethane and other higher boiling chlorohydrocarbons one of a group of compounds consisting of saturated monocarboxylic acids having from 2 to 6 carbon atoms, anhydrides of these same acids and saturated and unsaturated tertiary alcohols having from 4 to about 8 carbon atoms.

Acids useful as extractive solvents are acetic, propanoic, butanoic, 2-methyl propanoic, pentanoic, trimethyl ethanoic, 2-methyl butanoic, hexanoic, and the like. The anhydrides of the above acids are also useful. Thus, for example, acetic acid anhydride, propanoic acid anhydride and the like are useful as extractants in an extractive distillation for removing 1,1,1-trichloroethane from ethylene dichloride and other higher boiling chlorohydrocarbons.

In like manner the saturated and unsaturated tertiary alcohols are useful when employed as extractants for the separation of methyl chloroform from ethylene dichloride. Thus, tertiary alcohols such as 2-methyl-2-propanol, 2-methyl-2-butanol, 2-ethyl-2-butanol, 2-methyl-3-buten-2-ol, 2-methyl-4-penten-2-ol, 3-methyl-4-penetene-3-ol, 2-methyl-3-butyn-2-ol, 2-methyl-4-pentyn-2-ol, 3-methyl-4-pentyn-3-ol and the like are useful extractants.

Any of the above compounds may be employed as extractants providing that they neither react under the conditions of distillation nor form azeotropes with any components of the solvent mixture.

The extractants are employed in amounts of from about 25 to about 85 weight percent in the extraction column based on the amount of 1,1,1-trichloroethane present. Since relatively small amounts of the extractive solvent are removed with the methyl chloroform, it is necessary to add only that amount lost to the feed to the extraction column. The extractive solvent in the bottoms can be separated from the chlorohydrocarbons and recycled to the extraction.

Ordinarily, in a commercial operation the purified methyl chloroform is continuously removed from the top of the extraction column and the higher boiling chlorohydrocarbons continuously removed from the bottom. The extractant, if it is useful as an inhibitor or is not deleterious in the utilization of the methylchloroform, is allowed to remain in the purified solvent. If it is desired to remove it, a simple distillation can be performed and the extractant recycled. Likewise, the extractant is removed from the EDC and/or other chlorohydrocarbons and recycled to the extraction column.

The following examples show a preferred mode of operation of the present invention in which the extracting agent is continuously added to the 1,1,1-trichloroethane-chlorohydrocarbon mixture contained within a zone. In a commercial operation, the 1,1,1-trichloroethane enriched product is continuously distilled from the upper portion of the zone while a residue is continuously withdrawn from the lower portion of the zone. This technique is particularly applicable to the separation of 1,1,1-trichloroethane from 1,2-dichloroethane or for separation of 1,1,1-trichloroethane from other chlorinated hydrocarbons such as for the separation of 1,1,1-trichloroethane from reaction mixtures resultant in the manufacture of 1,1,1-trichloroethane by cochlorination of ethyl chloride and 1,1-dichloroethane.

The improvement in which the present invention resides is that of separating 1,1,1-trichloroethane from ethylene dichloride by employing in an extractive distillation one of a group of compounds consisting of saturated and unsaturated tertiary alcohols, organic acids and organic anhydrides as the extractant.

EXAMPLE 1

The apparatus employed in the process of this invention consisted of two 30-tray glass, vacuum-jacketed Oldershaw distillation columns joined one atop the other. At the 60th tray a feed point was inserted and another 15-tray glass, vacuum-jacketed Oldershaw column joined at this point. At the bottom of the entire column was a 2-liter reboiler flask. The reboiler was charged with 500 ml. of 1,1,1-trichloroethane containing 5% by weight ethylene dichloride (EDC, 1,2-dichloroethane). The reboiler was heated and the still lined-out at 5:1 reflux ratio. Samples of overhead and bottoms were taken and then t-amyl alcohol was pumped in at the feedpoint at the rate of 1 ml/min. After about 1 hour, or a sufficient time to insure equilibrium, samples of overhead and bottoms were taken. A nearly complete removal of the EDC was accomplished as shown by the results in the table below:

| Sample | 5:1 Reflux - 75 Tray - 60 cc/hr t-amyl alc. | | |
|---|---|---|---|
| | EDC mole % | α-Tri mole % | t-amyl alcohol mole % |
| Overhead | 2.28 | 97.72 | 0 |
| Bottoms | 6.84 | 93.16 | 0 |
| Overhead | 0.07 | 91.81 | 8.12 |
| Bottoms | 7.01 | 83.26 | 9.73 |

EXAMPLE 2

The method of Example 1 was repeated except for the use of acetic anhydride as the extractive solvent in place of the t-amyl alcohol. Results are shown below:

| Sample | 5:1 Reflux - 75 Tray - 60 cc/hr Acetic Anhydrile | | |
|---|---|---|---|
| | EDC mole % | α-Tri mole % | Acetic Anhydrile % |
| Overhead | 1.57 | 98.43 | 0 |
| Bottoms | 4.92 | 95.08 | 0 |
| Overhead | 0.32 | 99.68 | —* |

*not determined

EXAMPLE 3

The procedure of Example 1 was repeated except that 2-methyl-3-butyn-2-ol was employed in place of the t-amyl alcohol as the extractive solvent. Results are shown below:

| Sample | 5:1 Reflux - 75 Tray - 60 cc/hr Alc. | | |
|---|---|---|---|
| | EDC mole % | α-Tri mole % | 2-Methyl-3-Butyne-2-ol |
| Overhead | 3.48 | 96.52 | 0 |
| Bottoms | 9.34 | 90.66 | 0 |
| Overhead | 0.10 | 85.86 | 14.04 |

In all the above examples the extractant remaining in the 1,1,1-trichloroethane is removed therefrom by a simple distillation. As is well known to the art the amount of extractant left in the 1,1,1-trichloroethane will depend upon the design of the extraction, e.g., the number of trays above the entry point of the extractant. Thus, a column of optimum design may obviate a separate distillation of the 1,1,1-trichloroethane from the extractant.

We claim:

1. In a method of purifying 1,1,1-trichloroethane from mixtures thereof with higher boiling chlorohydrocarbons by extractive distillation with an auxiliary solvent the improvement of employing as the auxiliary solvent an organic compound selected from the group consisting of saturated and unsaturated tertiary alcohols, organic monocarboxylic acids and organic monocarboxylic acid anhydrides.

2. The method of claim 1 wherein the tertiary alcohol contains from 4 to 8 carbon atoms and the organic acid contains from 2 to 6 carbon atoms and the anhydride contains from 4 to 12 carbon atoms.

3. The method of claim 1 in which the higher boiling hydrocarbon is 1,2-dichloroethane.

4. The method of claim 1 wherein the auxiliary solvent is separated from the higher boiling chlorohydrocarbons and recycled to the distillation.

5. The method of claim 1 wherein the purified 1,1,1-trichloroethane is further distilled to remove the auxiliary solvent.

6. A method of purifying 1,1,1-trichloroethane from a mixture of the same with other higher boiling chlorohydrocarbons which comprises distilling said mixture with an organic compound which will increase the volatility of the 1,1,1-trichloroethane with respect to the other chlorinated hydrocarbons, and wherein said organic compound is selected from the group consisting of saturated and unsaturated tertiary alcohols, organic monocarboxylic acids and anhydrides of organic monocarboxylic acids.

* * * * *

UNITED STATES PATENT AND TRADEMARK OFFICE
CERTIFICATE OF CORRECTION

PATENT NO. : 3,989,601
DATED : Nov. 2, 1976
INVENTOR(S) : Theodore S. Boozalis, et al.

It is certified that error appears in the above-identified patent and that said Letters Patent are hereby corrected as shown below:

Col. 1, in the footnote labeled ** in the table, line 56, before "=isobutyl acetate" insert --IBA--.

Col. 4, Example 2, in the heading of the Table, line 37, the word "acetic Anhydrile" should be --Acetic Anhydride--.

Signed and Sealed this

First Day of February 1977

[SEAL]

Attest:

RUTH C. MASON
*Attesting Officer*

C. MARSHALL DANN
*Commissioner of Patents and Trademarks*